United States Patent [19]

Kaprelian et al.

[11] 4,406,620
[45] Sep. 27, 1983

[54] FACEBOW SWIVEL

[75] Inventors: George Kaprelian, Sunnyvale; Joseph Monfredo; Melvin Meyerson, both of San Diego, all of Calif.

[73] Assignee: Johnson and Johnson, Brunswick, N.J.

[21] Appl. No.: 433,768

[22] Filed: Oct. 12, 1982

[51] Int. Cl.³ .............................................. A61C 7/00
[52] U.S. Cl. ...................................................... 433/5
[58] Field of Search ............................................. 433/5

[56] References Cited

U.S. PATENT DOCUMENTS 741,687 10/1903 MacDowell .......................... 433/5
4,038,754 8/1977 Armstrong .......................... 433/5

Primary Examiner—Robert Peshock
Attorney, Agent, or Firm—Townsend and Townsend

[57] ABSTRACT

A facebow swivel is mounted to the bent distal end of an inner bow of a facebow. The swivel includes a pivot mount and an L-shaped pivot member. The pivot mount includes a pair of short parallel tube segments attached along their outer surfaces. One leg of the L-shaped swivel member is pivotally mounted within one of the tubes. The swivel is mounted to the bent distal end of the inner bow by inserting the distal end into the other tube. The swivel is then secured to the distal end, such as by crimping the tube onto the distal end.

11 Claims, 3 Drawing Figures

U.S. Patent      Sep. 27, 1983      4,406,620
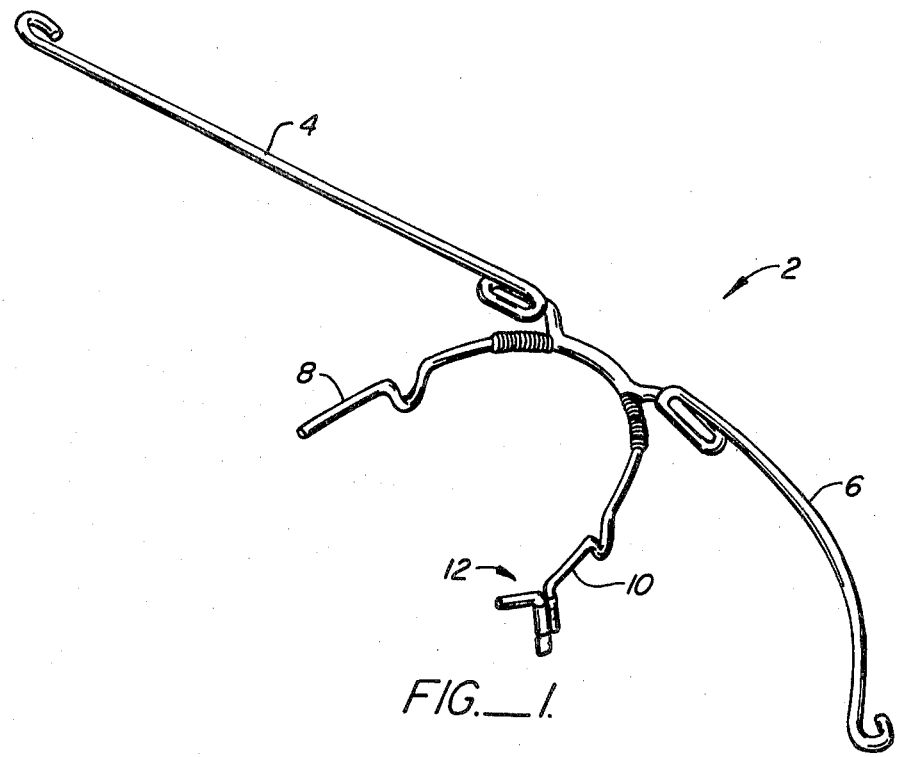
FIG._1.
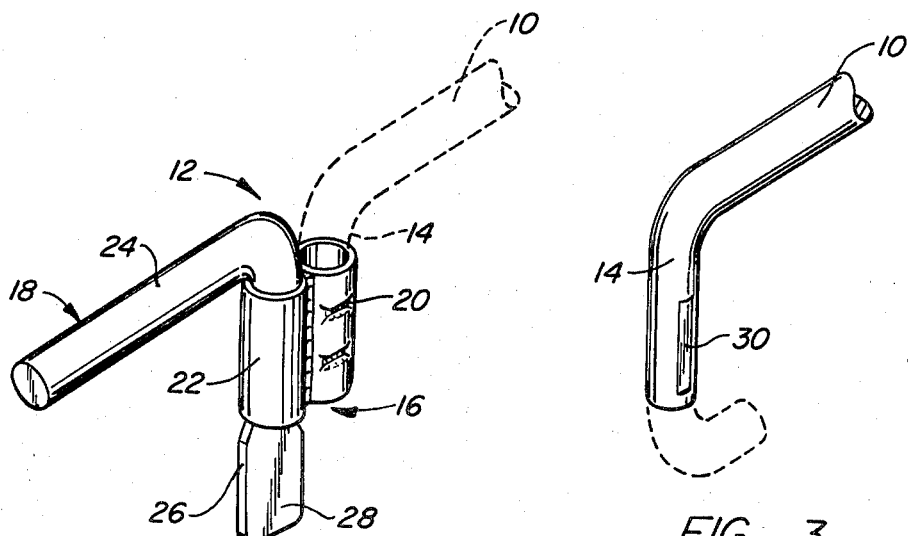
FIG._2.
FIG._3.

FACEBOW SWIVEL

DESCRIPTION

BACKGROUND OF THE INVENTION

In the practice of orthodontics sometimes molars on one side of the patient's mouth move faster than molars on the other side. At other times molars on one side may be in the proper position at the beginning of treatment. In either case the orthodontist wants to apply force only to the molars which need to be moved.

Many facebow designs have been used to try to eliminate applying force to a properly positioned molar. One known technique is to use a swivel near the distal end of the inner bow on the side next to the molars which are in the proper position. The resulting facebow is called a unilateral facebow since it applies force mainly on one side. The side on which the molars are in the proper position is called the non-force side. The purpose of the swivel is to reduce or eliminate the transmission of force to the molars on the non-force side to reduce or eliminate their displacement during treatment.

The prior art method used by the orthodontist to fashion the force breaking swivel typically proceeds as follows. First the orthodontist bends the distal end of the non-force inner bow downwardly at about a 90° angle. Using a small hand-grinder, flats are ground on the lateral sides of the downwardly extending distal end. A length of tubing is scored with a triangular file so that it can be fractured and broken off at the proper length. The end of the tubing is then bent over to partially fracture it at the score mark. Using the still attached main portion of the tubing as a handle, the end of a thin foil strip, having a width about equal to the length of the tube segment, is soldered to the outside of the tube segment. The foil strip is then trimmed to be about as long as it is wide.

This foil strip is then wrapped around the downwardly extending bent distal end of the inner bow and is soldered to it. Care must be taken to assure that the tube segment does not become filled with solder and that it is properly positioned. The main portion of the tubing is usually broken away from the tube segment before the last mentioned soldering step. The distal end of the inner bow, with the tube segment attached, is smoothed to remove the rough edges and is then buffed.

The end of a length of wire is then bent into an L-shape. The main length of the wire is passed through the top of the tube segment until the corner bend is reached. The main length of wire is then bent back over to form a semi-circular curve to keep the generally L-shaped swivel member from falling out of the tube segment. Finally, the main length of the wire is cut to the desired length and the cut end is filed and smoothed.

The main drawback with this prior art method is that it takes a relatively experienced practitioner from 10 to 20 minutes to fashion such a swivel. In addition some orthodontists may not use a force breaking swivel because of their lack of familiarity with the above fabrication procedure.

SUMMARY OF THE INVENTION

A facebow swivel is mounted to the distal end, which is bent downwardly at a right angle, of the inner bow of a facebow. The swivel includes a pair of short parallel tube segments attached along their outer surfaces. One leg of an L-shaped swivel member is pivotally mounted within one of the tubes. The swivel member is secured within the tube such as by flattening the end of the one leg.

The swivel is mounted to the bent distal end of the inner bow by inserting the bent end into the inner tube. The swivel is secured to the bent distal end of the inner bow such as by crimping the tube onto it.

The primary advantage of the present invention is that it allows an orthodontist to simply and quickly modify most standard facebows to apply force to only the molars which need to be moved. The practitioner need not spend the time custom fashioning swivels for each patient so time and cost are reduced. Since the user no longer needs to cut any pieces of material, sharp edges can be eliminated during the manufacture of the swivel for increased patient comfort.

Other features and advantages of the present invention will appear from the following description in which the preferred embodiment has been set forth in detail in conjunction with the accompanying drawing.

BRIEF DESCRIPTION OF THE DRAWING

FIG. 1 is a perspective view of a facebow incorporating the swivel of the invention.

FIG. 2 is an enlarged perspective view of the swivel of FIG. 1.

FIG. 3 is an enlarged perspective view of the bent distal end of the non-force inner bow of FIG. 1.

DETAILED DESCRIPTION OF THE PREFERRED EMBODIMENT

Referring now to the figures, facebow 2 includes a pair of outer bows 4, 6 and a pair of inner bows 8, 10. A swivel 12 is mounted to the distal end 14, which has been bent downwardly at a right angle, of inner bow 10. Swivel 12 is mounted to the distal end of the inner bow on the non-force side of facebow 2. That is, the molars adjacent the distal end of inner bow 8 are those which need to be moved while the molars adjacent non-force inner bow 10 do not need to be moved. In accord with this procedure, outer bow 4, which is on the force side of facebow 2, is usually straightened somewhat as shown in FIG. 1. Thus when attached to standard headgear, more force is applied to outer bow 4, and thus inner bow 8, than to outer bow 6 and inner bow 10. Swivel 12 supplies a link or break along inner bow 10 to further reduce the force applied to its associated molar.

Swivel 12 includes generally a pivot mount 16 and an L-shaped swivel member 18. Pivot mount 16 includes an inner tube 20 and an outer tube 22 joined along their parallel outer surfaces.

Member 18 includes a first leg 24 and a second leg 26. Second leg 26 is pivotally mounted within outer tube 22. Leg 26 includes a flattened end 28 to retain member 18 within outer tube 22.

The swivel of the present invention can be mounted to most standard facebows. To do so distal end 14 is bent downwardly at about a 90° angle. Inner tube 20 is then inserted over distal end 14 until swivel member 18 is generally aligned with inner bow 10. Inner tube 20 is then secured to distal end 14, typically by crimping using wire cutters. For better retention the lateral sides of distal end 14 may be provided with flats 30, such as with a hand grinder, prior to mounting swivel 12 as shown in FIG. 3. Other methods for mounting swivel 12 to distal end 14, such as by soldering or brazing or by applying an adhesive, may be used as well.

Although inner tube 20 is typically non-rotatably mounted to distal end 14, it may be desired to secure swivel 12 to inner bow 10 to allow rotation of both swivel member 18 and distal end 14 within their respective outer and inner tubes 22, 20. This may be accomplished by extending distal end past the bottom of inner tube 20 and then bending the tip of distal end 14 to keep swivel 12 from falling off distal end 14. Such a configuration is shown by dashed lines in FIG. 3.

Other modifications and variations to the disclosed embodiment can be made without departing from the subject of the invention as defined in the following claims.

We claim:

1. A facebow swivel for mounting to the bent distal end of an inner bow of a facebow comprising:
    a pivot mount including parallel inner and outer tubes joined along their parallel outer surfaces;
    an L-shaped swivel member having first and second legs, said second leg of said swivel member pivotally housed within said outer tube; and
    means for retaining said second leg within said outer tube.

2. The facebow swivel of claim 1 wherein said retaining means comprises an enlarged end of said second leg external of said outer tube.

3. The facebow swivel of claim 2 wherein said enlarged end is flattened.

4. A method for producing a unilateral facebow from a standard facebow of the type including inner bows having distal ends, the method comprising:
    bending the distal end of the inner bow on the non-force side of the facebow approximately 90°;
    mounting a facebow swivel to the bent distal end of the inner bow, the facebow swivel comprising an L-shaped swivel member and a pivot mount, the pivot mount having parallel inner and outer tubes joined along their adjacent sides, the swivel member having first and second legs, the second leg pivotally housed within the outer tube; and
    securing said bent distal end within said inner tube.

5. The method of claim 4 wherein said securing step includes the step of crimping said inner tube onto said bent distal end.

6. The method of claim 5 further comprising the step of forming a flattened surface on said distal end prior to said securing step.

7. The method of claim 4 wherein said securing step non-rotatably secures said bent distal end within said inner tube.

8. A unilateral facebow of the type including outer bows and inner bows, the facebow comprising:
    the non-force inner bow having an L-shaped bent distal end;
    a swivel mounted to the distal end of the non-force inner bow, the swivel comprising:
        a pivot mount including parallel inner and outer tubes joined along their parallel outer surfaces, said inner tube adapted for receipt of said bent distal end;
        an L-shaped swivel member having first and second legs, said second leg of said swivel member pivotally housed within said outer tube; and
        means for retaining said second leg within said outer tube; and
    means for securing said inner tube to said bent distal end of said one inner bow.

9. The facebow of claim 8 wherein said bent distal end is bent downwardly at a right angle.

10. The unilateral facebow of claim 8 wherein said retaining means includes an enlarged, flattened end of said second leg.

11. The unilateral facebow of claim 8 wherein said securing means includes means for non-rotatably securing said inner tube to said bent distal end of said one inner bow.

* * * * *